US009517184B2

(12) United States Patent
Branconier et al.

(10) Patent No.: US 9,517,184 B2
(45) Date of Patent: Dec. 13, 2016

(54) FEEDING TUBE WITH INSUFFLATION DEVICE AND RELATED METHODS THEREFOR

(75) Inventors: Glen Branconier, North Attleboro, MA (US); Michael C. Dorsey, Edwardsville, IL (US); Kelly M. Davis, Chesterfield, MO (US); David Rork Swisher, St. Charles, MO (US); John P. Moran, Herculaneum, MO (US)

(73) Assignee: Covidien LP, Mansfield, MA (US)

(*) Notice: Subject to any disclaimer, the term of this patent is extended or adjusted under 35 U.S.C. 154(b) by 628 days.

(21) Appl. No.: 13/606,179

(22) Filed: Sep. 7, 2012

(65) Prior Publication Data

US 2014/0074014 A1    Mar. 13, 2014

(51) Int. Cl.
| A61M 29/00 | (2006.01) |
| A61J 15/00 | (2006.01) |
| A61M 13/00 | (2006.01) |
| A61B 1/00  | (2006.01) |

(52) U.S. Cl.
CPC .......... *A61J 15/0026* (2013.01); *A61J 15/0003* (2013.01); *A61M 13/003* (2013.01); *A61B 1/00068* (2013.01)

(58) Field of Classification Search
CPC ...... A61J 15/003; A61J 15/00; A61J 15/0026; A61J 15/004; A61B 1/0005
USPC  604/26, 31, 32, 98.02, 103.1, 99.2; 600/109
See application file for complete search history.

(56) References Cited

U.S. PATENT DOCUMENTS

| 3,633,758 A | 1/1972  | Morse et al. |
| 3,788,304 A | 1/1974  | Takahashi |
| 4,146,019 A | 3/1979  | Bass et al. |
| 4,253,447 A | 3/1981  | Moore et al. |
| 4,301,790 A | 11/1981 | Bol et al. |
| D267,019 S  | 11/1982 | Goldsmith |
| 4,392,485 A | 7/1983  | Hiltebrandt |
| 4,491,865 A | 1/1985  | Danna et al. |

(Continued)

FOREIGN PATENT DOCUMENTS

| EP | 0299240 A2 | 1/1989 |
| EP | 1707102 A1 | 10/2006 |

(Continued)

OTHER PUBLICATIONS

1000 Icons, Symbols + Pictograms: Visual Communication for Every Language, Rockport Publishers, Gloucester, MA 2006, p. 89.

(Continued)

*Primary Examiner* — Theodore Stigell
*Assistant Examiner* — Tiffany Legette (57) ABSTRACT

A feeding tube assembly for insertion and delivery of nutrients into an alimentary canal is disclosed. A method of facilitating the use of the feeding tube with an insufflation device is also disclosed. The feeding tube assembly has a feeding tube with opposite proximal and distal ends, a feeding passage extending between the proximal and distal ends, an outlet proximate the distal end and in fluid communication with the feeding passage, a port at the proximal end and in fluid communication with the outlet; and an air insufflation device fluidly connectable to the port comprising a compressible air bulb having a bulb inlet and a bulb outlet; an inlet check valve at the bulb inlet, an outlet check valve at the bulb outlet, and a relief valve fluidly connected to the bulb outlet.

13 Claims, 10 Drawing Sheets

(56) References Cited

U.S. PATENT DOCUMENTS

| | | | |
|---|---|---|---|
| D281,081 S | 10/1985 | Zwissler et al. |
| 4,616,630 A | 10/1986 | Arakawa |
| 4,621,284 A | 11/1986 | Nishioka et al. |
| 4,769,014 A | 9/1988 | Russo |
| 4,782,819 A | 11/1988 | Adair |
| 4,809,680 A | 3/1989 | Yabe |
| 4,846,153 A | 7/1989 | Berci |
| 4,919,651 A | 4/1990 | Doane |
| 4,996,975 A | 3/1991 | Nakamura |
| 5,025,778 A | 6/1991 | Silverstein et al. |
| 5,059,182 A * | 10/1991 | Laing ........................... 604/142 |
| 5,131,380 A | 7/1992 | Heller et al. |
| 5,168,863 A | 12/1992 | Kurtzer |
| 5,187,579 A | 2/1993 | Hiyama |
| 5,220,198 A | 6/1993 | Tsuji |
| 5,242,394 A * | 9/1993 | Tremulis ................... 604/96.01 |
| 5,285,778 A | 2/1994 | Mackin |
| 5,297,477 A * | 3/1994 | Phillips ................... A47J 43/14 434/81 |
| 5,329,940 A | 7/1994 | Adair |
| 5,334,150 A | 8/1994 | Kaali |
| 5,353,783 A | 10/1994 | Nakao et al. |
| 5,400,771 A | 3/1995 | Pirak et al. |
| 5,409,480 A | 4/1995 | Uram |
| 5,423,311 A | 6/1995 | Snoke et al. |
| 5,435,339 A * | 7/1995 | Hayes ................... F16K 31/528 137/315.04 |
| 5,469,254 A | 11/1995 | Konomura |
| 5,526,928 A | 6/1996 | Yabe et al. |
| 5,527,261 A | 6/1996 | Monroe et al. |
| 5,604,531 A | 2/1997 | Iddan et al. |
| 5,610,828 A | 3/1997 | Kodosky et al. |
| 5,636,625 A | 6/1997 | Miyagi et al. |
| 5,638,819 A | 6/1997 | Manwaring et al. |
| 5,645,519 A | 7/1997 | Lee et al. |
| 5,665,064 A | 9/1997 | Bodicky et al. |
| 5,676,635 A | 10/1997 | Levin |
| D390,666 S | 2/1998 | Lagerlof |
| D391,247 S | 2/1998 | Wanishi et al. |
| 5,720,293 A | 2/1998 | Quinn et al. |
| D393,850 S | 4/1998 | Norton |
| 5,740,802 A | 4/1998 | Nafis et al. |
| 5,772,693 A | 6/1998 | Brownlee |
| D398,595 S | 9/1998 | Baer et al. |
| 5,800,342 A | 9/1998 | Lee et al. |
| 5,817,015 A | 10/1998 | Adair |
| 5,830,121 A | 11/1998 | Enomoto et al. |
| 5,840,013 A | 11/1998 | Lee et al. |
| 5,848,691 A | 12/1998 | Morris et al. |
| 5,873,816 A | 2/1999 | Kagawa et al. |
| D406,894 S | 3/1999 | Menhennett et al. |
| 5,896,166 A | 4/1999 | D'Alfonso et al. |
| 5,908,294 A | 6/1999 | Schick et al. |
| 5,913,816 A | 6/1999 | Sanders et al. |
| 5,929,901 A | 7/1999 | Adair et al. |
| D412,748 S | 8/1999 | Nabarro |
| 5,932,035 A | 8/1999 | Koger et al. |
| 5,938,603 A | 8/1999 | Ponzi |
| 5,941,816 A | 8/1999 | Barthel et al. |
| D414,870 S | 10/1999 | Saltzstein et al. |
| 5,967,988 A | 10/1999 | Briscoe et al. |
| 5,986,693 A | 11/1999 | Adair et al. |
| 5,989,230 A | 11/1999 | Frassica |
| 5,989,231 A | 11/1999 | Snow et al. |
| 6,004,263 A | 12/1999 | Nakaichi et al. |
| 6,043,839 A | 3/2000 | Adair et al. |
| 6,053,313 A | 4/2000 | Farrell et al. |
| D426,204 S | 6/2000 | Maio et al. |
| 6,099,354 A | 8/2000 | Troyan |
| 6,115,523 A | 9/2000 | Choi et al. |
| 6,117,071 A | 9/2000 | Ito et al. |
| 6,120,435 A | 9/2000 | Eino |
| 6,134,003 A | 10/2000 | Tearney et al. |
| 6,198,963 B1 | 3/2001 | Haim et al. |
| 6,237,604 B1 | 5/2001 | Burnside et al. |
| 6,245,029 B1 | 6/2001 | Fujita et al. |
| 6,275,255 B1 | 8/2001 | Adair et al. |
| D447,569 S | 9/2001 | Baily et al. |
| 6,310,642 B1 | 10/2001 | Adair et al. |
| 6,322,495 B1 | 11/2001 | Gravenstein et al. |
| 6,322,498 B1 | 11/2001 | Gravenstein et al. |
| 6,339,446 B1 | 1/2002 | Miyoshi |
| D455,760 S | 4/2002 | Platz |
| D456,027 S | 4/2002 | Boehler et al. |
| 6,364,827 B1 | 4/2002 | Irion et al. |
| D459,477 S | 6/2002 | Stocks et al. |
| 6,447,444 B1 | 9/2002 | Avni et al. |
| 6,458,076 B1 | 10/2002 | Pruitt |
| 6,462,770 B1 | 10/2002 | Cline et al. |
| 6,468,212 B1 | 10/2002 | Scott et al. |
| D465,789 S | 11/2002 | Platz |
| D466,519 S | 12/2002 | Shim et al. |
| D470,505 S | 2/2003 | Platz |
| 6,520,916 B1 | 2/2003 | Brennen |
| D471,226 S | 3/2003 | Gray |
| D471,227 S | 3/2003 | Gray |
| 6,543,447 B2 | 4/2003 | Pacey |
| 6,547,757 B1 | 4/2003 | Kranz et al. |
| 6,550,475 B1 | 4/2003 | Oldfield |
| 6,553,241 B2 | 4/2003 | Mannheimer et al. |
| 6,554,765 B1 | 4/2003 | Yarush et al. |
| 6,565,506 B2 | 5/2003 | Ishizuka |
| 6,585,639 B1 | 7/2003 | Kotmel et al. |
| 6,612,980 B2 | 9/2003 | Chen et al. |
| 6,623,480 B1 | 9/2003 | Kuo et al. |
| 6,626,828 B2 | 9/2003 | Dohi et al. |
| D483,872 S | 12/2003 | Cruz et al. |
| 6,655,377 B2 | 12/2003 | Pacey |
| 6,692,430 B2 | 2/2004 | Adler |
| 6,692,432 B1 | 2/2004 | Yarush et al. |
| 6,712,756 B1 | 3/2004 | Kura et al. |
| 6,712,760 B2 | 3/2004 | Sano et al. |
| D491,954 S | 6/2004 | Platz et al. |
| 6,761,561 B2 | 7/2004 | Mandelkern et al. |
| 6,814,727 B2 | 11/2004 | Mansouri-Ruiz |
| 6,860,611 B2 | 3/2005 | Gentz |
| 6,862,467 B2 | 3/2005 | Moore et al. |
| 6,875,169 B2 | 4/2005 | Berci et al. |
| 6,890,298 B2 | 5/2005 | Berci et al. |
| D506,195 S | 6/2005 | Leveridge et al. |
| 6,902,529 B2 | 6/2005 | Onishi et al. |
| 6,909,795 B2 | 6/2005 | Tecotzky et al. |
| 6,911,027 B1 | 6/2005 | Edwards et al. |
| 6,929,600 B2 | 8/2005 | Hill |
| 6,945,929 B2 | 9/2005 | Ando |
| 6,960,161 B2 | 11/2005 | Amling et al. |
| 6,966,876 B2 | 11/2005 | Irion et al. |
| 6,986,738 B2 | 1/2006 | Glukhovsky et al. |
| D514,558 S | 2/2006 | Nagel et al. |
| 7,011,285 B2 | 3/2006 | Wang et al. |
| 7,022,075 B2 | 4/2006 | Grunwald et al. |
| 7,033,316 B2 | 4/2006 | Takahashi |
| 7,044,909 B2 | 5/2006 | Berci et al. |
| 7,048,687 B1 | 5/2006 | Reuss et al. |
| 7,063,660 B2 | 6/2006 | Chen et al. |
| 7,063,663 B2 | 6/2006 | Kazakevich |
| 7,090,661 B2 | 8/2006 | Morris et al. |
| 7,126,581 B2 | 10/2006 | Burk et al. |
| 7,131,873 B2 | 11/2006 | Miyake et al. |
| 7,151,956 B2 | 12/2006 | Satoh et al. |
| 7,166,537 B2 | 1/2007 | Jacobsen et al. |
| 7,223,232 B2 | 5/2007 | Mizuno |
| 7,245,959 B1 | 7/2007 | Wasicek |
| 7,270,650 B2 | 9/2007 | Morris et al. |
| 7,273,452 B2 | 9/2007 | Barbato et al. |
| 7,288,074 B2 | 10/2007 | Swain et al. |
| 7,289,139 B2 | 10/2007 | Amling et al. |
| 7,297,105 B2 | 11/2007 | Mackin |
| D558,351 S | 12/2007 | Diener et al. |
| 7,303,528 B2 | 12/2007 | Couvillon, Jr. |
| 7,304,277 B2 | 12/2007 | Weber |
| 7,316,646 B2 | 1/2008 | Amling et al. |
| D562,456 S | 2/2008 | Scruggs et al. |
| 7,366,562 B2 | 4/2008 | Dukesherer et al. |

(56) References Cited

U.S. PATENT DOCUMENTS

| | | |
|---|---|---|
| 7,373,005 B2 | 5/2008 | Venkataraman |
| 7,391,606 B2 | 6/2008 | Chen et al. |
| 7,404,794 B2 | 7/2008 | Scholly |
| 7,413,543 B2 | 8/2008 | Banik et al. |
| 7,423,496 B2 | 9/2008 | Scheuermann |
| D582,916 S | 12/2008 | Wada |
| 7,471,310 B2 | 12/2008 | Amling et al. |
| 7,491,167 B2 | 2/2009 | Ogino et al. |
| 7,497,825 B2 | 3/2009 | Sarwari |
| D591,423 S | 4/2009 | Diener et al. |
| 7,530,946 B2 | 5/2009 | Hartwick |
| 7,547,277 B2 | 6/2009 | Wiklof et al. |
| D598,109 S | 8/2009 | Collins et al. |
| 7,585,273 B2 | 9/2009 | Adler et al. |
| 7,591,780 B2 | 9/2009 | Jacobsen et al. |
| 7,596,402 B2 | 9/2009 | Duerk et al. |
| D601,582 S | 10/2009 | Chaudhri et al. |
| 7,599,730 B2 | 10/2009 | Hunter et al. |
| 7,604,627 B2 | 10/2009 | Kojouri |
| 7,628,752 B2 | 12/2009 | Yamamoto et al. |
| 7,651,277 B2 | 1/2010 | Gurreri et al. |
| D609,350 S | 2/2010 | Hickey et al. |
| 7,660,453 B2 | 2/2010 | Lang |
| 7,662,151 B2 | 2/2010 | Crompton, Jr. et al. |
| 7,672,491 B2 | 3/2010 | Krishnan et al. |
| D613,411 S | 4/2010 | Collins et al. |
| D614,634 S | 4/2010 | Nilsen |
| 7,697,972 B2 | 4/2010 | Verard et al. |
| D615,199 S | 5/2010 | Zimmerli et al. |
| 7,713,189 B2 | 5/2010 | Hanke |
| 7,720,521 B2 | 5/2010 | Chang et al. |
| 7,740,578 B2 | 6/2010 | Little |
| D621,515 S | 8/2010 | Chua et al. |
| 7,773,122 B2 | 8/2010 | Irion et al. |
| 7,780,650 B2 | 8/2010 | Frassica et al. |
| 7,787,939 B2 | 8/2010 | Jacobsen et al. |
| 7,789,823 B2 | 9/2010 | Kato et al. |
| 7,805,188 B2 | 9/2010 | Brushey |
| 7,806,121 B2 | 10/2010 | Bodduluri |
| 7,831,070 B1 | 11/2010 | Cheng et al. |
| 7,846,091 B2 | 12/2010 | Fulghum |
| 7,850,370 B2 | 12/2010 | Murano |
| 7,860,555 B2 | 12/2010 | Saadat |
| 7,860,556 B2 | 12/2010 | Saadat |
| 7,879,004 B2 | 2/2011 | Seibel et al. |
| 7,896,802 B2 | 3/2011 | Otawara |
| 7,898,085 B2 | 3/2011 | Fujimori |
| 7,901,348 B2 | 3/2011 | Soper et al. |
| 7,901,353 B2 | 3/2011 | Vayser et al. |
| 7,914,448 B2 | 3/2011 | Bob et al. |
| 7,922,654 B2 | 4/2011 | Boutillette et al. |
| 7,930,016 B1 | 4/2011 | Saadat |
| D638,943 S | 5/2011 | Daniel |
| 7,942,814 B2 | 5/2011 | Remijan et al. |
| 7,976,459 B2 | 7/2011 | Laser |
| 7,978,891 B2 | 7/2011 | Assmann et al. |
| 7,985,213 B2 | 7/2011 | Parker |
| D643,936 S | 8/2011 | Oonuma et al. |
| D644,246 S | 8/2011 | Matas |
| 7,993,264 B2 | 8/2011 | Crank |
| 7,998,062 B2 | 8/2011 | Gilboa |
| 8,016,749 B2 | 9/2011 | Clerc et al. |
| 8,049,061 B2 | 11/2011 | Ehrenreich et al. |
| 8,050,746 B2 | 11/2011 | Saadat et al. |
| 8,052,596 B2 | 11/2011 | Kim |
| 8,069,420 B2 | 11/2011 | Plummer |
| D650,484 S | 12/2011 | Shinohara et al. |
| 8,075,477 B2 | 12/2011 | Nakamura et al. |
| 8,075,583 B2 | 12/2011 | Lee et al. |
| 8,135,195 B2 | 3/2012 | Mahesh et al. |
| 8,139,296 B2 | 3/2012 | Ito |
| D657,059 S | 4/2012 | Geijsen et al. |
| D658,295 S | 4/2012 | Geijsen et al. |
| 8,152,560 B2 | 4/2012 | Malstron et al. |
| 8,152,712 B2 | 4/2012 | Abe |
| 8,160,676 B2 | 4/2012 | Gielen et al. |
| 8,162,820 B2 | 4/2012 | Moore |
| 8,162,824 B2 | 4/2012 | Vayser et al. |
| 8,162,825 B2 | 4/2012 | Matsumoto et al. |
| D659,836 S | 5/2012 | Bensch et al. |
| 8,172,864 B2 | 5/2012 | Wu |
| 8,175,680 B2 | 5/2012 | Panescu |
| 8,183,510 B2 | 5/2012 | Venezia et al. |
| 8,194,121 B2 | 6/2012 | Blumzvig et al. |
| 8,194,122 B2 | 6/2012 | Amling et al. |
| 8,199,187 B2 | 6/2012 | Knapp, II et al. |
| 8,206,289 B2 | 6/2012 | Zen |
| 8,206,374 B2 | 6/2012 | Duane et al. |
| 8,211,128 B1 * | 7/2012 | Facundus ............ A61B 17/1114 128/898 |
| 8,214,015 B2 | 7/2012 | Macaulay et al. |
| 8,216,185 B2 | 7/2012 | Berger |
| 8,228,369 B2 | 7/2012 | Kojima et al. |
| 8,231,522 B2 | 7/2012 | Endo et al. |
| 8,235,887 B2 | 8/2012 | Bayer et al. |
| 8,241,199 B2 | 8/2012 | Maschke |
| 8,262,559 B2 | 9/2012 | Krattiger |
| 8,262,622 B2 | 9/2012 | Gonzales et al. |
| 8,265,732 B2 | 9/2012 | Besz et al. |
| 8,280,205 B2 | 10/2012 | Erdman et al. |
| 8,285,362 B2 | 10/2012 | Dietz et al. |
| 8,292,874 B2 | 10/2012 | Stivland et al. |
| 8,297,440 B2 | 10/2012 | Schmidt et al. |
| 8,308,637 B2 | 11/2012 | Ishigami et al. |
| 8,314,835 B2 | 11/2012 | Kanzaki et al. |
| 8,317,689 B1 | 11/2012 | Remijan et al. |
| 8,336,541 B2 | 12/2012 | Schwartz et al. |
| 8,360,964 B2 | 1/2013 | Ertas |
| 8,386,023 B2 | 2/2013 | Furnish |
| 8,388,376 B2 | 3/2013 | Yamamoto et al. |
| 8,390,995 B2 | 3/2013 | Wang et al. |
| 8,400,767 B2 | 3/2013 | Yeom et al. |
| 8,403,836 B2 | 3/2013 | Shimotsu |
| 8,408,269 B2 | 4/2013 | Fengler et al. |
| 8,408,815 B2 | 4/2013 | Lin et al. |
| 8,409,081 B2 | 4/2013 | Takahashi |
| 8,421,626 B2 | 4/2013 | Downie et al. |
| 8,425,405 B2 | 4/2013 | Mitani et al. |
| 8,444,802 B2 | 5/2013 | Lee et al. |
| 8,454,578 B2 | 6/2013 | Leeflang et al. |
| 8,471,392 B2 | 6/2013 | Kojima |
| 8,480,404 B2 | 7/2013 | Savitsky |
| 8,485,966 B2 | 7/2013 | Robertson |
| 8,485,967 B2 | 7/2013 | Takahashi et al. |
| 8,486,023 B2 | 7/2013 | Pyles |
| 8,496,001 B2 | 7/2013 | Schermeier et al. |
| 8,496,574 B2 | 7/2013 | Trusty et al. |
| 8,496,580 B2 | 7/2013 | Dotan et al. |
| 8,512,232 B2 | 8/2013 | Rothberg et al. |
| 8,514,556 B2 | 8/2013 | Huang et al. |
| 8,547,689 B2 | 10/2013 | Moser |
| 8,556,806 B2 | 10/2013 | Farr |
| 8,568,159 B2 | 10/2013 | Noda et al. |
| 8,573,824 B2 | 11/2013 | Komukai et al. |
| 8,574,192 B2 | 11/2013 | Haarala et al. |
| 8,585,586 B2 | 11/2013 | Yamaguchi et al. |
| 8,587,710 B2 | 11/2013 | Jeon |
| 8,591,407 B2 | 11/2013 | Wendlandt et al. |
| D695,410 S | 12/2013 | Becker |
| 8,597,179 B2 | 12/2013 | Kokubo |
| 8,599,264 B2 | 12/2013 | Schmidt |
| 8,600,133 B2 | 12/2013 | Buelow et al. |
| 8,602,967 B2 | 12/2013 | Robertson |
| 8,602,979 B2 | 12/2013 | Kitano |
| 8,606,347 B2 | 12/2013 | Besz et al. |
| 2002/0007108 A1 | 1/2002 | Chen et al. |
| 2002/0093563 A1 | 7/2002 | Cline et al. |
| 2002/0126960 A1 | 9/2002 | Gurreri |
| 2003/0055314 A1 | 3/2003 | Petitto et al. |
| 2003/0060678 A1 | 3/2003 | Watai et al. |
| 2003/0112921 A1 | 6/2003 | Lang et al. |
| 2004/0111012 A1 | 6/2004 | Whitman |
| 2004/0111081 A1 | 6/2004 | Whitman et al. |
| 2004/0133074 A1 | 7/2004 | Chen et al. |

(56) References Cited

U.S. PATENT DOCUMENTS

| | | |
|---|---|---|
| 2004/0162487 A1 | 8/2004 | Klingenbeck-Regn et al. |
| 2004/0165833 A1 | 8/2004 | Betker et al. |
| 2004/0171914 A1 | 9/2004 | Avni |
| 2004/0181431 A1 | 9/2004 | Kuth et al. |
| 2004/0199088 A1 | 10/2004 | Bakos et al. |
| 2004/0237048 A1 | 11/2004 | Tojo et al. |
| 2004/0239760 A1 | 12/2004 | Shoji et al. |
| 2004/0252871 A1 | 12/2004 | Tecotzky et al. |
| 2005/0021182 A1 | 1/2005 | Wang et al. |
| 2005/0038318 A1 | 2/2005 | Goldwasser |
| 2005/0054895 A1 | 3/2005 | Hoeg et al. |
| 2005/0073017 A1 | 4/2005 | Kim |
| 2005/0154262 A1 | 7/2005 | Banik et al. |
| 2005/0177024 A1 | 8/2005 | Mackin |
| 2005/0192477 A1 | 9/2005 | Forster et al. |
| 2005/0200698 A1 | 9/2005 | Amling et al. |
| 2005/0203338 A1 | 9/2005 | Couvillon, Jr. et al. |
| 2005/0216041 A1 | 9/2005 | Okada et al. |
| 2005/0250983 A1 | 11/2005 | Tremaglio et al. |
| 2005/0251013 A1 | 11/2005 | Krishnan et al. |
| 2005/0277808 A1 | 12/2005 | Sonnenschein et al. |
| 2006/0020171 A1 | 1/2006 | Gilreath |
| 2006/0025650 A1 | 2/2006 | Gavriely |
| 2006/0117185 A1 | 6/2006 | Oguri et al. |
| 2006/0122460 A1 | 6/2006 | Kamali |
| 2006/0171586 A1 | 8/2006 | Georgescu et al. |
| 2006/0171856 A1 | 8/2006 | Jehle |
| 2006/0224040 A1 | 10/2006 | Khait et al. |
| 2006/0235274 A1 | 10/2006 | Forster et al. |
| 2006/0264918 A1 | 11/2006 | Cook et al. |
| 2006/0287576 A1 | 12/2006 | Tsuji et al. |
| 2007/0049794 A1 | 3/2007 | Glassenberg et al. |
| 2007/0075208 A1 | 4/2007 | Chen |
| 2007/0113204 A1 | 5/2007 | Son et al. |
| 2007/0162095 A1 | 7/2007 | Kimmel et al. |
| 2007/0167682 A1 | 7/2007 | Goldfarb et al. |
| 2007/0225561 A1 | 9/2007 | Watanabe et al. |
| 2007/0232882 A1 | 10/2007 | Glossop et al. |
| 2007/0235626 A1 | 10/2007 | Mamizuka et al. |
| 2007/0276216 A1 | 11/2007 | Beyar et al. |
| 2008/0021273 A1 | 1/2008 | MacKin |
| 2008/0037850 A1 | 2/2008 | Assmann et al. |
| 2008/0045800 A2 | 2/2008 | Farr |
| 2008/0062624 A1 | 3/2008 | Regen et al. |
| 2008/0074492 A1 | 3/2008 | Iwasaki |
| 2008/0077043 A1* | 3/2008 | Malbrain et al. ............. 600/547 |
| 2008/0081949 A1 | 4/2008 | Gilad |
| 2008/0091065 A1 | 4/2008 | Oshima et al. |
| 2008/0108869 A1 | 5/2008 | Sanders et al. |
| 2008/0123922 A1 | 5/2008 | Gielen et al. |
| 2008/0139896 A1 | 6/2008 | Baumgart |
| 2008/0140020 A1* | 6/2008 | Shirley ................ A61M 39/10 604/240 |
| 2008/0172006 A1* | 7/2008 | Hicks ........................... 604/249 |
| 2008/0236575 A1 | 10/2008 | Chuda |
| 2008/0240527 A1 | 10/2008 | Keller |
| 2008/0255416 A1 | 10/2008 | Gilboa |
| 2008/0275301 A1 | 11/2008 | Lubowski et al. |
| 2008/0281157 A1 | 11/2008 | Miyagi et al. |
| 2008/0281351 A1* | 11/2008 | Croushorn ......... A61B 17/1325 606/202 |
| 2008/0294000 A1 | 11/2008 | Iwamoto |
| 2008/0294007 A1 | 11/2008 | Takada |
| 2008/0300456 A1 | 12/2008 | Irion et al. |
| 2008/0319391 A1 | 12/2008 | Jackson |
| 2009/0030276 A1 | 1/2009 | Saadat et al. |
| 2009/0030283 A1 | 1/2009 | Freystein et al. |
| 2009/0043167 A1 | 2/2009 | Leiner |
| 2009/0046906 A1 | 2/2009 | Wohlgemuth et al. |
| 2009/0054803 A1 | 2/2009 | Saadat et al. |
| 2009/0060425 A1 | 3/2009 | Aronson |
| 2009/0062609 A1 | 3/2009 | Suda |
| 2009/0069694 A1 | 3/2009 | Amundson et al. |
| 2009/0082625 A1 | 3/2009 | Gono |
| 2009/0099417 A1 | 4/2009 | Hartwick |
| 2009/0105538 A1 | 4/2009 | Van Dam et al. |
| 2009/0118577 A9 | 5/2009 | Snay et al. |
| 2009/0118580 A1 | 5/2009 | Sun et al. |
| 2009/0137893 A1 | 5/2009 | Seibel et al. |
| 2009/0143648 A1 | 6/2009 | Sutoh et al. |
| 2009/0143651 A1 | 6/2009 | Kallback et al. |
| 2009/0149705 A1 | 6/2009 | Tani et al. |
| 2009/0149706 A1 | 6/2009 | Yamazaki et al. |
| 2009/0155750 A1 | 6/2009 | Abe |
| 2009/0161927 A1 | 6/2009 | Mori et al. |
| 2009/0163769 A1 | 6/2009 | Robertson et al. |
| 2009/0167851 A1 | 7/2009 | Miller et al. |
| 2009/0171148 A1 | 7/2009 | Lu et al. |
| 2009/0177032 A1 | 7/2009 | Garibaldi et al. |
| 2009/0187425 A1 | 7/2009 | Thompson |
| 2009/0198102 A1 | 8/2009 | Chen et al. |
| 2009/0198106 A1 | 8/2009 | Ichihashi |
| 2009/0209826 A1 | 8/2009 | Sanders et al. |
| 2009/0213140 A1 | 8/2009 | Ito et al. |
| 2009/0214089 A1 | 8/2009 | Stookey |
| 2009/0216080 A1 | 8/2009 | Nakamura |
| 2009/0225159 A1 | 9/2009 | Schneider et al. |
| 2009/0234220 A1 | 9/2009 | Maschke |
| 2009/0237497 A1 | 9/2009 | Iinuma et al. |
| 2009/0253955 A1 | 10/2009 | Akiba |
| 2009/0259097 A1 | 10/2009 | Thompson |
| 2009/0268019 A1 | 10/2009 | Ishii et al. |
| 2009/0275799 A1 | 11/2009 | Saadat et al. |
| 2009/0299137 A1 | 12/2009 | Gal et al. |
| 2009/0299363 A1 | 12/2009 | Saadat et al. |
| 2009/0303316 A1 | 12/2009 | Iwasaki et al. |
| 2009/0316975 A1 | 12/2009 | Kunz et al. |
| 2009/0318757 A1 | 12/2009 | Singh |
| 2009/0318758 A1 | 12/2009 | Farr et al. |
| 2009/0318797 A1 | 12/2009 | Hadani |
| 2009/0318798 A1 | 12/2009 | Singh et al. |
| 2009/0326321 A1 | 12/2009 | Jacobsen et al. |
| 2009/0326481 A1* | 12/2009 | Swisher ................ A61M 39/10 604/246 |
| 2010/0010302 A1 | 1/2010 | Hadani |
| 2010/0010334 A1 | 1/2010 | Bleich et al. |
| 2010/0016757 A1 | 1/2010 | Greenburg et al. |
| 2010/0022824 A1 | 1/2010 | Cybulski et al. |
| 2010/0030020 A1 | 2/2010 | Sanders et al. |
| 2010/0030057 A1 | 2/2010 | Gavriely et al. |
| 2010/0030138 A1* | 2/2010 | Kantsevoy ......... A61M 25/0116 604/95.03 |
| 2010/0047733 A1 | 2/2010 | Nahlieli |
| 2010/0063352 A1 | 3/2010 | Matsuura |
| 2010/0063355 A1 | 3/2010 | Matsuura |
| 2010/0073470 A1 | 3/2010 | Takasaki |
| 2010/0081873 A1 | 4/2010 | Tanimura et al. |
| 2010/0085273 A1 | 4/2010 | Nakayama |
| 2010/0121139 A1 | 5/2010 | OuYang et al. |
| 2010/0121142 A1 | 5/2010 | OuYange et al. |
| 2010/0121155 A1 | 5/2010 | OuYange et al. |
| 2010/0174141 A1 | 7/2010 | Gilad et al. |
| 2010/0179384 A1 | 7/2010 | Hoeg et al. |
| 2010/0191053 A1 | 7/2010 | Garcia et al. |
| 2010/0198009 A1 | 8/2010 | Farr et al. |
| 2010/0204546 A1 | 8/2010 | Hassidov et al. |
| 2010/0204561 A1 | 8/2010 | Saadat et al. |
| 2010/0211005 A1* | 8/2010 | Edwards ................ A61M 5/002 604/82 |
| 2010/0230140 A1 | 9/2010 | Huang et al. |
| 2010/0249507 A1 | 9/2010 | Prisco et al. |
| 2010/0249512 A1 | 9/2010 | McKinley et al. |
| 2010/0249639 A1 | 9/2010 | Bhatt |
| 2010/0280316 A1 | 11/2010 | Dietz et al. |
| 2010/0286475 A1 | 11/2010 | Robertson |
| 2010/0286477 A1 | 11/2010 | OuYang et al. |
| 2010/0305503 A1* | 12/2010 | Fang et al. ................. 604/96.01 |
| 2011/0004058 A1 | 1/2011 | Oneda et al. |
| 2011/0009694 A1 | 1/2011 | Schultz et al. |
| 2011/0015614 A1 | 1/2011 | Rykhus, Jr. et al. |
| 2011/0034769 A1 | 2/2011 | Adair et al. |
| 2011/0036965 A1 | 2/2011 | Zhang et al. |
| 2011/0037876 A1 | 2/2011 | Talbert et al. |
| 2011/0098530 A1 | 4/2011 | Yamane |

(56) References Cited

U.S. PATENT DOCUMENTS

| | | |
|---|---|---|
| 2011/0113329 A1 | 5/2011 | Pusateri |
| 2011/0130627 A1 | 6/2011 | McGrail et al. |
| 2011/0130631 A1 | 6/2011 | Geisser et al. |
| 2011/0137117 A1 | 6/2011 | Jacobsen et al. |
| 2011/0137118 A1 | 6/2011 | Huang |
| 2011/0137127 A1 | 6/2011 | Schwartz et al. |
| 2011/0144481 A1 | 6/2011 | Feer et al. |
| 2011/0152613 A1 | 6/2011 | Zubiate et al. |
| 2011/0160535 A1 | 6/2011 | Bayer et al. |
| 2011/0160537 A1 | 6/2011 | Chen |
| 2011/0172687 A1 | 7/2011 | Woodruff et al. |
| 2011/0196204 A1 | 8/2011 | Setty et al. |
| 2011/0201882 A1 | 8/2011 | Schwartz et al. |
| 2011/0218400 A1 | 9/2011 | Ma et al. |
| 2011/0245605 A1 | 10/2011 | Jacobsen et al. |
| 2011/0245606 A1 | 10/2011 | Hayashi et al. |
| 2011/0245607 A1 | 10/2011 | Hayashi et al. |
| 2011/0245608 A1 | 10/2011 | Takahashi et al. |
| 2011/0249025 A1 | 10/2011 | Mitani et al. |
| 2011/0249106 A1 | 10/2011 | Makino et al. |
| 2011/0251456 A1 | 10/2011 | Jacobsen et al. |
| 2011/0255760 A1 | 10/2011 | Mahesh et al. |
| 2011/0257478 A1 | 10/2011 | Kleiner et al. |
| 2011/0263938 A1 | 10/2011 | Levy |
| 2011/0270295 A1 | 11/2011 | Litvack et al. |
| 2011/0275894 A1 | 11/2011 | Mackin |
| 2011/0282144 A1 | 11/2011 | Gettman |
| 2011/0288372 A1 | 11/2011 | Petersen |
| 2011/0289441 A1 | 11/2011 | Venon et al. |
| 2011/0294361 A1 | 12/2011 | Schrader |
| 2011/0295061 A1 | 12/2011 | Haramaty et al. |
| 2011/0295072 A1 | 12/2011 | Boulais et al. |
| 2011/0301415 A1 | 12/2011 | Motai et al. |
| 2011/0311116 A1 | 12/2011 | Benn |
| 2012/0006950 A1 | 1/2012 | Vandiver |
| 2012/0010469 A1 | 1/2012 | Boyer |
| 2012/0029279 A1 | 2/2012 | Kucklick |
| 2012/0029290 A1 | 2/2012 | Nishijima |
| 2012/0058457 A1 | 3/2012 | Savitsky |
| 2012/0062714 A1 | 3/2012 | Liu et al. |
| 2012/0065469 A1 | 3/2012 | Allyn et al. |
| 2012/0071723 A1 | 3/2012 | Ishigami et al. |
| 2012/0078174 A1 | 3/2012 | Tai et al. |
| 2012/0084680 A1 | 4/2012 | Gimpl et al. |
| 2012/0086790 A1 | 4/2012 | Takahira et al. |
| 2012/0108960 A1 | 5/2012 | Halmann et al. |
| 2012/0130171 A1 | 5/2012 | Barak et al. |
| 2012/0131488 A1 | 5/2012 | Karlsson et al. |
| 2012/0136212 A1 | 5/2012 | Komukai et al. |
| 2012/0172665 A1 | 7/2012 | Allyn et al. |
| 2012/0190922 A1* | 7/2012 | Kaku ............... A61B 1/00009 600/109 |
| 2012/0197078 A1 | 8/2012 | Stanley |
| 2012/0197086 A1 | 8/2012 | Morris et al. |
| 2012/0203065 A1 | 8/2012 | Higgins et al. |
| 2012/0242814 A1 | 9/2012 | Kubala et al. |
| 2012/0316515 A1 | 12/2012 | Terry |
| 2013/0007668 A1 | 1/2013 | Liu et al. |
| 2013/0027533 A1 | 1/2013 | McDowell |
| 2013/0030249 A1 | 1/2013 | Vazales et al. |
| 2013/0035589 A1 | 2/2013 | Besz et al. |
| 2013/0066150 A1 | 3/2013 | Lee et al. |
| 2013/0067397 A1 | 3/2013 | Kirschner et al. |
| 2013/0103000 A1 | 4/2013 | Vogelbaum et al. |
| 2013/0128020 A1 | 5/2013 | Fujimori |
| 2013/0155591 A1 | 6/2013 | Yamaguchi et al. |
| 2013/0162789 A1 | 6/2013 | Chou et al. |
| 2013/0169777 A1 | 7/2013 | Zen |
| 2013/0172678 A1 | 7/2013 | Kennedy, II et al. |
| 2013/0177222 A1 | 7/2013 | Tridandapani et al. |
| 2013/0184584 A1 | 7/2013 | Berkey |
| 2013/0184683 A1 | 7/2013 | Chow et al. |
| 2013/0188030 A1 | 7/2013 | Igarashi |
| 2013/0197484 A1 | 8/2013 | Seddon et al. |
| 2013/0198687 A1 | 8/2013 | Bird et al. |
| 2013/0216112 A1 | 8/2013 | Graessner |
| 2013/0231533 A1 | 9/2013 | Papademetriou et al. |
| 2013/0237755 A1 | 9/2013 | Singh |
| 2013/0245568 A1 | 9/2013 | Kerr |
| 2013/0250061 A1 | 9/2013 | Hofer |
| 2013/0250079 A1 | 9/2013 | Nakamura et al. |
| 2013/0253348 A1 | 9/2013 | Tremper |
| 2013/0265403 A1 | 10/2013 | Okawa et al. |
| 2013/0271588 A1 | 10/2013 | Kirma et al. |
| 2013/0303849 A1 | 11/2013 | Allyn et al. |
| 2013/0317300 A1 | 11/2013 | Berci et al. |
| 2013/0324968 A1 | 12/2013 | Klein |
| 2014/0052475 A1 | 2/2014 | Madan et al. |

FOREIGN PATENT DOCUMENTS

| | | |
|---|---|---|
| EP | 1709899 A1 | 10/2006 |
| EP | 1847214 A2 | 10/2007 |
| GB | 2448421 A | 10/2008 |
| JP | 54-049192 U | 4/1979 |
| JP | 08191440 | 7/1996 |
| JP | 2008194334 A | 8/2008 |
| JP | 2009056238 A | 3/2009 |
| WO | 0167964 A2 | 9/2001 |
| WO | 02/055126 A2 | 7/2002 |
| WO | 2005102175 A2 | 11/2005 |
| WO | 2006070360 A1 | 7/2006 |
| WO | 2006071948 A2 | 7/2006 |
| WO | 2009049322 A2 | 4/2009 |
| WO | 2009108854 A1 | 9/2009 |
| WO | 2010066788 A2 | 6/2010 |
| WO | 2010123858 A2 | 10/2010 |
| WO | 2011018812 A1 | 2/2011 |
| WO | 2011126812 A1 | 10/2011 |
| WO | 2012033936 A2 | 3/2012 |

OTHER PUBLICATIONS

Logo Lounge, by Bill Gardner and Catharine Fishel, Rockport Publishers, Goucester, MA 2003, p. 131.
Logo Lounge 2, by Bill Gardner and Catherine Fishel, Rockport Publishers, Gloucester, MA 2005, pp. 92 and 112.
Symbol Sourcebook, by Henry Dreyfuss, Van Nostrand Reinhold Company, New York, NY, 1972, p. 118.
Artyomov et al., "Image Sensors in Security and Medical Applications". International Journal "Information Theories & Applications", vol. 14, 2007. pp. 114-127.
Kfouri et al, "Toward a Miniaturized Wireless". IEEE Journal of Selected Topics in Quantum Electronics, vol. 14, No. 1, Jan./Feb. 2008, pp. 226-234.
International Search Report regarding corresponding PCT/US2013/055688, dated Nov. 18, 2013, 4 pages.
Written Opinion of the International Searching Authority, PCT/US2013/055688, dated Nov. 18, 2013, 4 pages.
International Preliminary Report on Patentability dated Mar. 19, 2015 in related International Application No. PCT/US2013/055688, 6 pages.
Examiner's Report dated Feb. 22, 2016 in related Canadian Application No. 2,883,678, 5 pages.
Australian Patent Examination Report No. 1 dated Nov. 10, 2015 in related Application No. 2013313246, 4 pages.

* cited by examiner

FEEDING TUBE WITH INSUFFLATION DEVICE AND RELATED METHODS THEREFOR

FIELD

The present invention relates feeding tubes and in particular to enteral feeding tubes comprising an air insufflation assembly.

BACKGROUND

Several medical procedures involve positioning a catheter, such as a feeding tube or endoscope, within a patient through the patient's nose, mouth, or other opening. In many procedures, accurately positioning the catheter is crucial to the success of the procedure and/or to the safety of the patient. For example, a nasogastric (NG) feeding tube may be inserted through the nose, past the throat, and down into the stomach, or past the stomach into the small bowels of the patient to deliver food to the patient via the tube. If the feeding tube is mistakenly positioned in the patient's lung, the feeding solution would be delivered to the patient's lung causing critical and possibly fatal results.

SUMMARY

One or more aspects of the invention can relate to a feeding tube assembly for insertion and delivery of nutrients into an alimentary canal of a subject. The feeding tube assembly can comprise a feeding tube having opposite proximal and distal ends, a feeding passage defined therein and extending between the proximal and distal ends, an outlet proximate the distal end and in fluid communication with the feeding passage, and a port disposed at the proximal end and in fluid communication with the outlet; and an air insufflation device fluidly connectable to one of the first and second ports, comprising a compressible air bulb having a bulb inlet and a bulb outlet; an inlet check valve disposed at the bulb inlet to unidirectionally allow air to flow into the bulb, an outlet check valve disposed at the bulb outlet to unidirectionally allow air to flow from the bulb, and a relief valve fluidly connected to the bulb outlet. In one or more embodiments pertinent to one or more aspects of the invention, the feeding tube assembly can further comprise an imaging assembly secured to the feeding tube proximate the distal end thereof. In one or more embodiments pertinent to one or more aspects of the invention, the feeding tube assembly can further comprise a conduit comprising opposite first and second conduit ends, and a conduit lumen defined therein, the conduit lumen fluidly connecting the first and second conduit ends; and a connector connected to the second conduit end and configured to fluidly connect to the feeding tube at the port thereof, the connector comprising a plurality of ribs each extending longitudinally about an outer surface of the connector. In one or more embodiments pertinent to one or more aspects of the invention, the feeding tube assembly can further comprise a relief valve having a valve member actuatable by a user for fluidly connecting the outlet to atmosphere. In further embodiments pertinent to one or more aspects of the invention, the relief valve comprises a cap securable to the valve member. The relief valve, in some cases, can be fluidly connected to the outlet through the feeding passage and the conduit. In yet further embodiments pertinent to one or more aspects of the invention, the relief valve comprises a valve passage fluidly connectable to the conduit lumen. The valve member can comprise a protrusion in the valve passage. In further embodiments pertinent to one or more aspects of the invention, the feeding tube assembly can further comprise an inlet adaptor at the proximal end of the feeding tube in fluid communication with the feeding passage. The connector can be an oral connector configured for sealed attachment to the inlet adaptor. In one or more embodiments pertinent to one or more aspects of the invention, the feeding tube is a nasogastric feeding tube.

One or ore aspects of the invention can be directed to a method of facilitating use of a feeding tube assembly for insertion into an alimentary canal of a subject, the feeding tube assembly comprising a feeding tube having opposite proximal and distal ends, a feeding passage extending between the proximal and distal ends, an outlet proximate the distal end and in fluid communication with the feeding passage, and a port at the proximal end and in fluid communication with the outlet through the feeding passage. The method can comprise providing an air insufflation device comprising a compressible air bulb having a bulb inlet and a bulb outlet, an inlet check valve disposed at the bulb inlet to unidirectionally allow air to flow into the bulb, an outlet check valve disposed at the bulb outlet to unidirectionally allow air to flow from the bulb, and a relief valve fluidly connectable to the outlet through the feeding passage. The feeding tube, in some embodiments pertinent to some methods of the invention, can comprise an imaging assembly configured to generate and transmit signals representative of images of the alimentary canal. In accordance with one or more aspects of the invention, the method can further comprise providing a conduit having a conduit lumen defined therein, a first conduit end and an opposite, second conduit end fluidly connected to the first conduit end through the conduit lumen; and providing a connector comprising a plurality of ribs, each of the plurality of ribs disposed equidistantly about an outer surface of the connector, the connector configured to removably connect to the feeding tube at the port, the connector further configured to connect to the conduit. In accordance with one or more aspects of the invention, the method can further comprise connecting the connector to the conduit at the second conduit end. In accordance with one or more aspects of the invention, the method can further comprise connecting the relief valve to the conduit, wherein the relief valve comprises a valve member actuatable by a user for fluidly connecting the outlet to atmosphere.

One or more aspects of the invention can be directed to an air insufflation device for use with a feeding tube at least partially inserted into an alimentary canal comprising a compressible air bulb having an inlet and an outlet; a check valve disposed at the inlet of the bulb for permitting air to enter the bulb at the inlet of the bulb and preventing air from exiting the bulb inlet; a relief valve attached to the outlet of the bulb, the valve having an inlet and an outlet; a conduit having a proximal end and a distal end, the proximal end being attached to the outlet of the relief valve; and a connector attached to the distal end of the conduit, the connector being configured for connecting the air insufflation device to a proximal end of the feeding tube, wherein compression of the bulb delivering air through the conduit and into the feeding tube to insufflate the alimentary canal. The connector can have ribs extending longitudinally along the connector and spaced circumferentially around the connector.

Other features pertinent to any of the assemblies, systems, components and subcomponents of the invention will be in part apparent and in part pointed out hereinafter.

BRIEF DESCRIPTION OF THE DRAWINGS

Corresponding reference characters indicate corresponding parts throughout the drawings.

DETAILED DESCRIPTION

One or more aspects of the invention provide a feeding tube connectable to a source of insufflation air. One or more further aspects of the invention can be directed to an insufflation assembly or providing such insufflation assemblies for use with one or more different feeding tubes from one or more different suppliers or manufacturers. One or more further aspects of the invention can be directed to providing one or more connectors for use with any of the various configurations of insufflation assemblies disclosed herein for use with one or more different feeding tubes from one or more different suppliers or manufacturers. One or more aspects of the invention can provide feeding tube assemblies comprising insufflation assemblies that involve a single user or operator. Further aspects of the invention can advantageously facilitate nasogastric insertion of a feeding tube allowing a single user or operator to perform contemporaneous insufflation and insertion operations.

Figure 1:
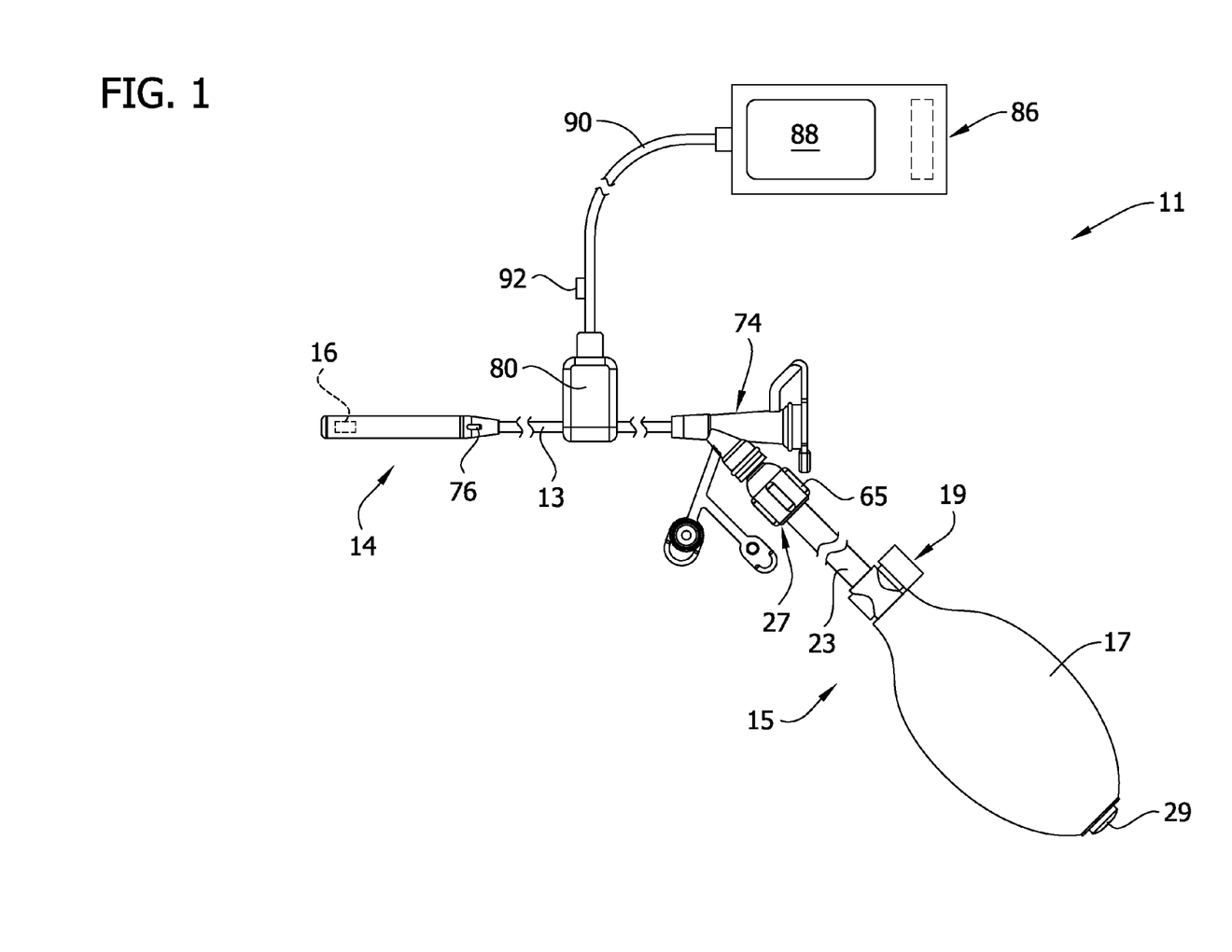
FIG. 1 is a schematic, fragmentary elevation of a feeding tube assembly in accordance with one or more aspects of the invention.
Figure 2:
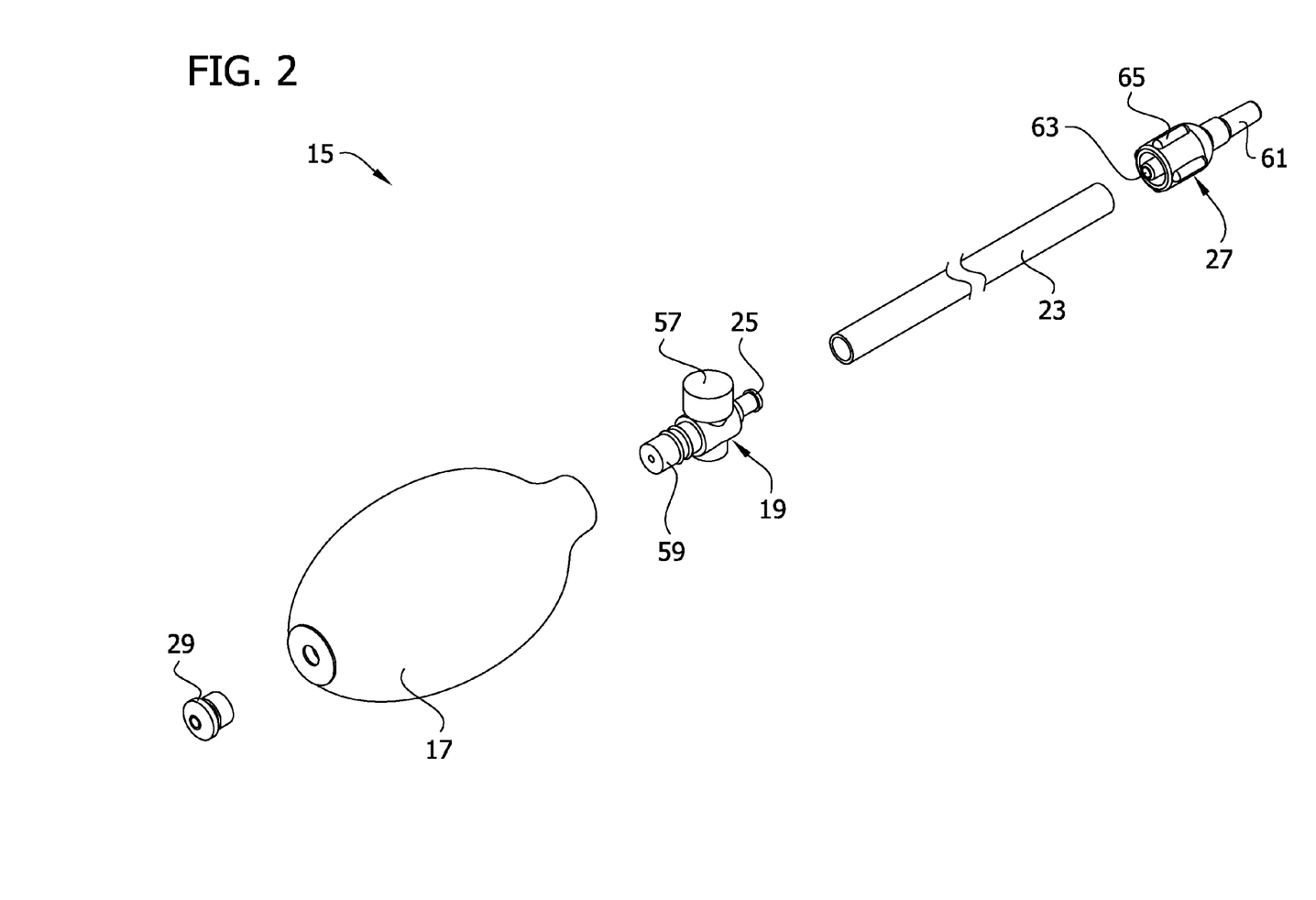
FIG. 2 is an exploded perspective of an air insufflation device of the feeding tube assembly, in accordance with one or more aspects of the invention.
Figure 3:
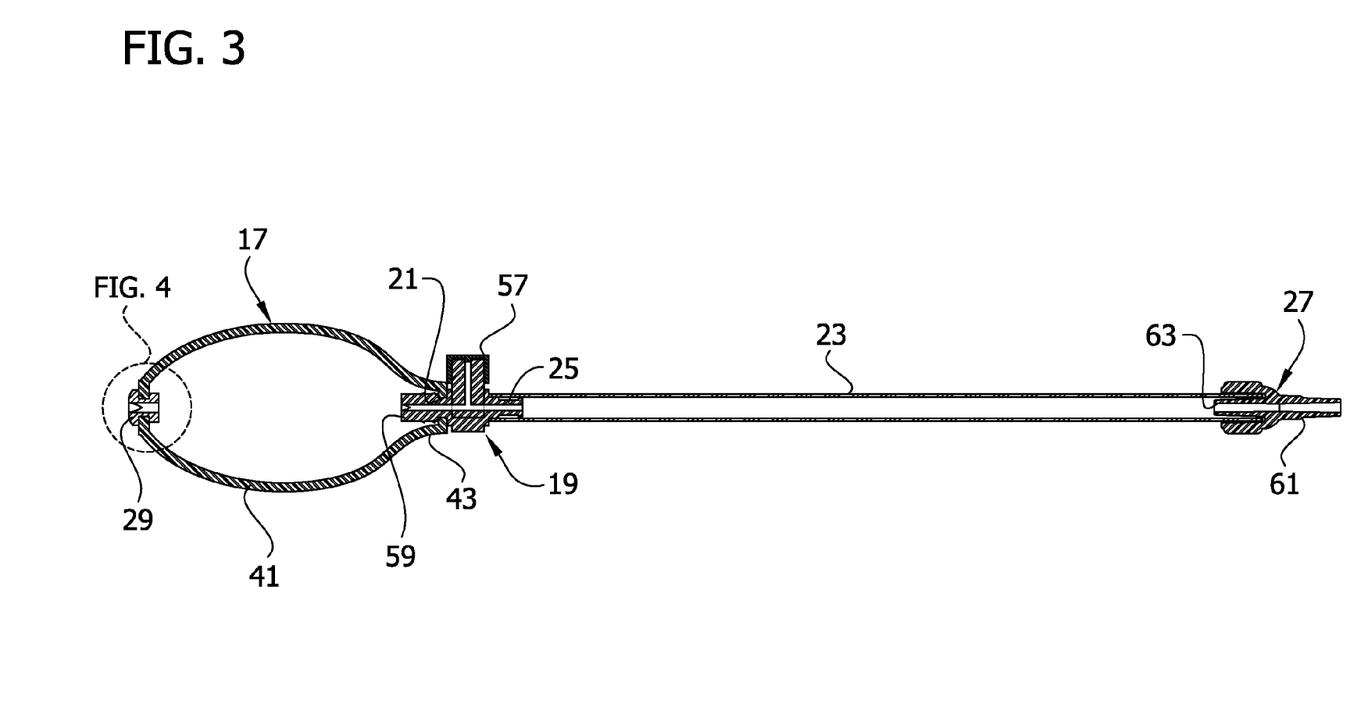
FIG. 3 is a longitudinal section of the air insufflation device, in accordance with one or more aspects of the invention.

Referring to FIGS. 1-3, a feeding tube assembly is generally indicated at 11. The assembly may comprise a feeding tube, generally indicated at 13, and an air insufflation device, generally indicated at 15, removably attachable to a proximal end of the feeding tube at a port thereof. The illustrated feeding tube 13 is a nasogastric feeding tube that may comprise an imaging assembly 14 including an imaging device 16 (e.g., a CCD or CMOS camera, or fiber optic, or other imaging device) adjacent its distal end to provide digital images of an alimentary canal, or a portion(s) thereof, of the subject as the feeding tube is inserted into the subject and after the feeding tube is positioned in the subject to facilitate confirmation of proper placement of the feeding tube assembly in the subject. During placement of the feeding tube 13, tissue of the alimentary canal (or other organ) may collapse around the distal end of the feeding tube, making it difficult to acquire meaningful images of the subject's anatomy during placement of the tube and when confirming placement of the tube. Accordingly, the air insufflation device 15 may be used to insufflate the alimentary canal to expand the alimentary canal and aid in the acquisition of meaningful images of the subject's anatomy.

Figure 4:
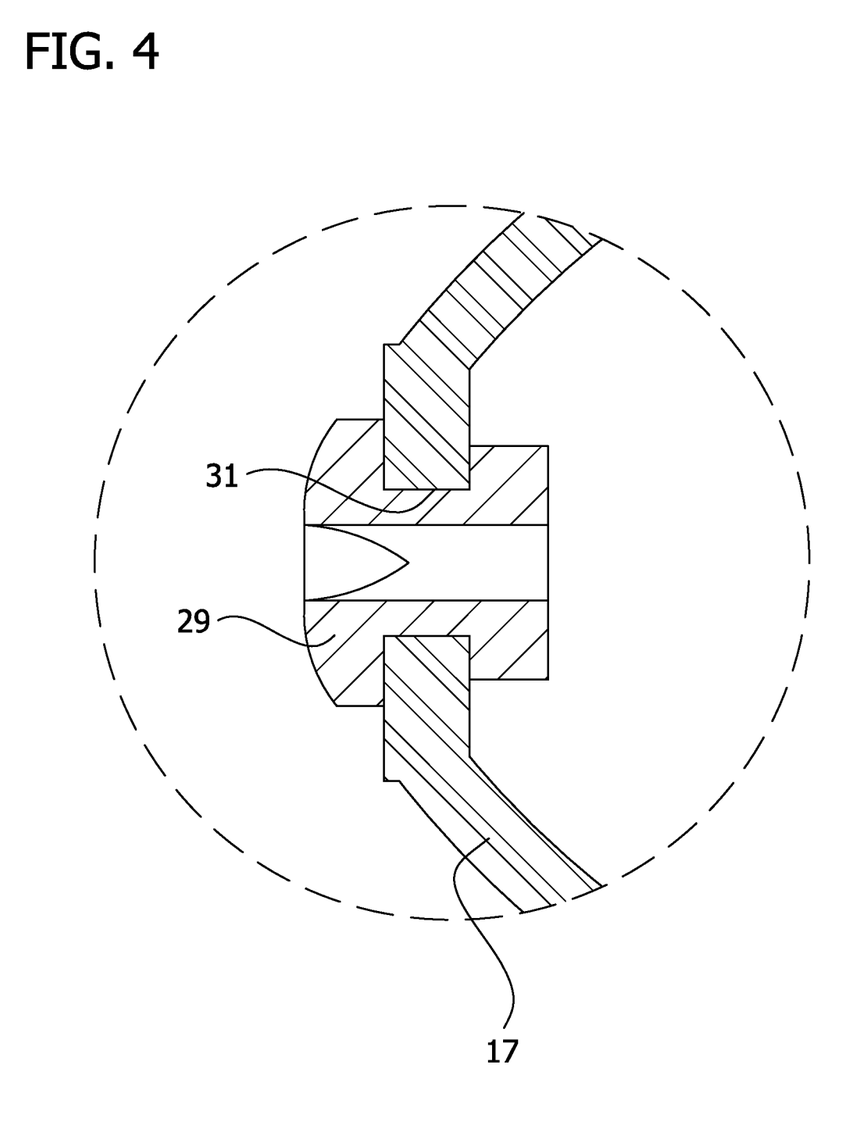
FIG. 4 is an enlarged detail of the section of FIG. 3, in accordance with one or more aspects of the invention.

The air insufflation device 15 may comprise a compressible air bulb 17, a relief valve, generally indicated at 19, attached to an outlet 21 (FIG. 3) of the bulb, a conduit 23 attached to a first connector portion 25 of the relief valve at a proximal end of the conduit, and a connector, generally indicated at 27, attached to a distal end of the conduit. A check valve 29 may be disposed at an inlet 31 (FIG. 4) of the air bulb 17 for permitting air into the bulb and inhibiting air from exiting the bulb at the inlet 31. The check valve 29 can be seated in the inlet 31 of the bulb 17 (FIG. 4). The check valve 29 typically only allows a one-way direction of airflow into the bulb 17 through the inlet 31. When the bulb 17 is compressed, air in the bulb can be expelled out of the outlet 21, through the relief valve 19 (which is closed to atmosphere), and into the conduit 23. When the bulb 17 is released, it returns to its uncompressed state, creating a vacuum within the bulb which draws air into the bulb through the check valve 29 at the inlet 31 to unidirectionally charge the bulb with air. After a subsequent compression of the bulb 17, air is exhausted through the outlet 21 and delivered into the conduit 23. When the air insufflation device 15 is attached to the feeding tube 13 and the feeding tube is at least partially inserted in the alimentary canal of a subject (FIGS. 9A and 9B), the air delivered to the conduit 23 can enter the feeding tube and insufflate (i.e., fill with air) the alimentary canal for at least partially expansion of the proximate region of the alimentary canal which can facilitate further insertion of the feeding tube and, in some cases, aids in the acquisition of meaningful images of the subject's anatomy by the imaging device 16.

Other variant embodiments can involve utilizing a relief valve that is fluidly connected or connectable to the outlet of the feeding tube through the feeding passage but is not directly fluidly connected to the bulb. For example, the relief valve can be connected to another port of the feeding tube assembly. Decoupling the relief valve from the bulb can allow individual and independent manipulation of components of the insufflation device. Further variants can involve directly coupling or fluidly connecting the bulb to a port of the feeding tube, without the use of a conduit. Thus, some configurations of the insufflation device can involve a bulb having an integrated connector disposed at an outlet thereof.

A second check valve 33 can be disposed at an outlet of the bulb and is typically configured to selectively, unidirectionally allow air to exhaust from the bulb through the outlet. The second check valve 33 can have the same or have similar configuration as check valve 29. Thus in some configurations, the second check valve 33 inhibits withdrawal of air from the alimentary canal into the bulb, in favor of introducing atmospheric or ambient air through the first check valve 29 during expansion of or the release of compressive force on the bulb.

The bulb 17 may comprise a bulbous portion 41 and a narrow portion 43 (FIG. 3). The bulb 17 can be formed of any suitable elastic material so that the bulb will automatically return to its uncompressed state after the bulb is compressed and released. In one embodiment, the bulb 17 is formed from rubber.

Figure 5:
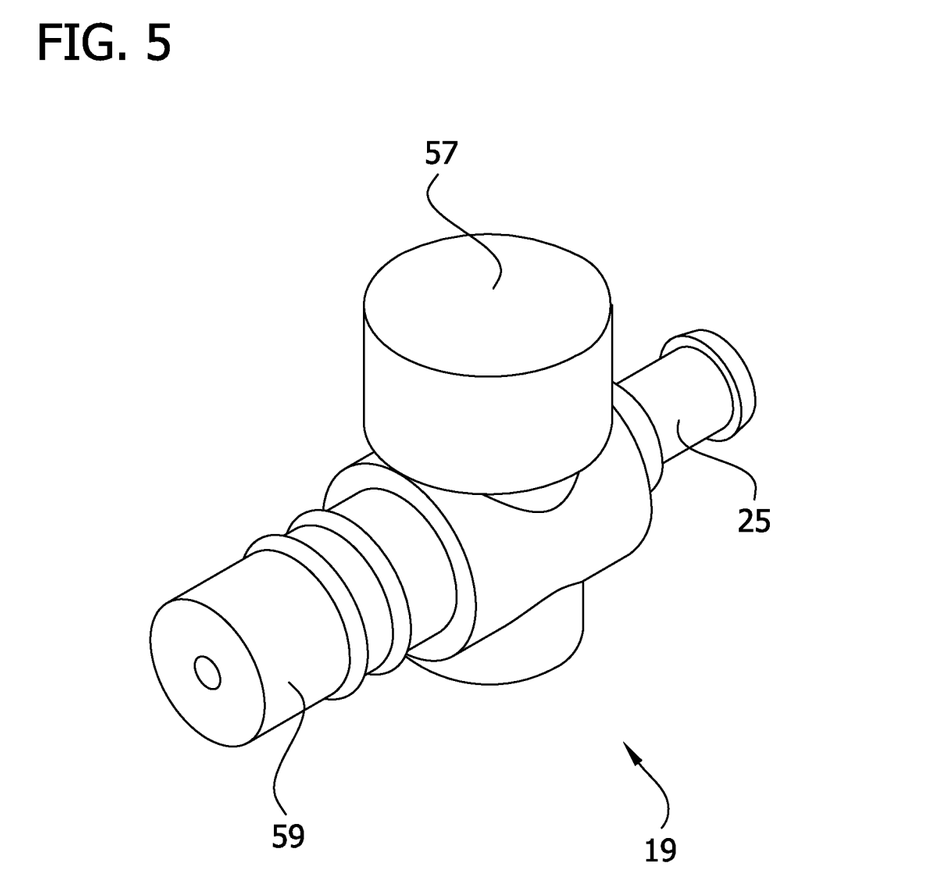
FIG. 5 is a perspective of a relief valve of the air insufflation device, in accordance with one or more aspects of the invention.
Figure 6:
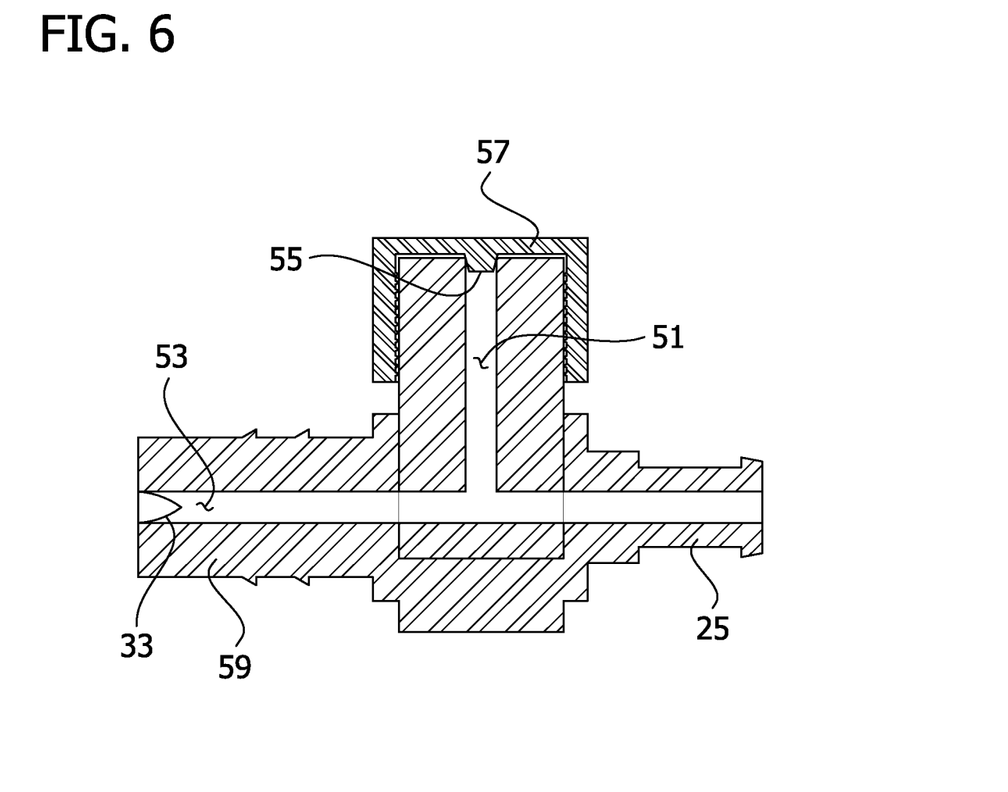
FIG. 6 is a section of the relief valve, in accordance with one or more aspects of the invention.

Referring to FIGS. 5 and 6, the relief valve 19 may comprise a valve body including a valve passage 51 and a fluid delivery passage 53. The valve passage 51 and fluid delivery passage 53 can be in fluid communication with each other. A valve member 55 is positionable between a seated position (FIG. 6), in which the relief valve 19 is closed and the valve passage 51 is closed to atmosphere or ambient pressure, and an unseated position (not shown), in which the relief valve is open and valve member is open to atmosphere. A rotatable cap 57 (e.g., a screw cap) carrying the valve member 55 is threadably mounted on the valve body and is rotatable to seat and unseat the valve member to open and close the relief valve 19. The valve member 55 may comprise a protrusion from the underside of the cap 57 that extends into the passage 51, particularly in the closed position. By screwing and unscrewing the cap 57 air in the alimentary canal can be release in short spurts to control the level of insufflation. Other valve configurations and arrangements may be used within the scope of the present invention. A second connector portion 59 of the relief valve 19 can extend proximally from the valve body and be received in the outlet 21 of the bulb 17. The fluid delivery passage 53 may extend through the relief valve 19 placing the bulb 17 in fluid communication with the conduit 23 (FIG. 3).

Figure 7:
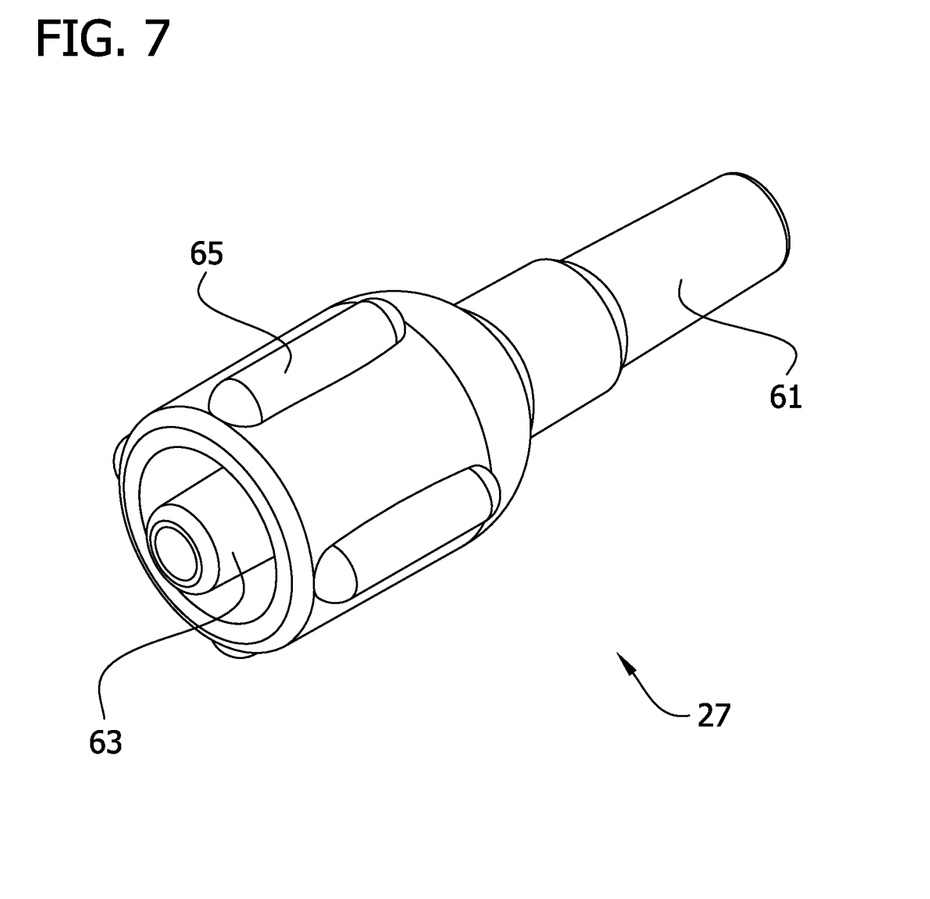
FIG. 7 is a perspective of a connector of the air insufflation device, in accordance with one or more aspects of the invention.

The conduit 23 may comprise an elongate tubular member. The illustrated connector 27 may comprise an oral connector having a distal end portion 61 for connecting to an inlet adapter 74 attached to a proximal end of the feeding tube 13 (FIGS. 1 and 7). A proximal end of the connector 27 can include a fitting 63 for attaching the connector to the distal end of the conduit 23 and ribs 65 extending longitudinally along the connector and spaced circumferentially around the connector. The conduit 23 and connector 27 may have other configurations. The air insufflation device 15 may also be disposable in that it is configured to be discarded after a single use rather than sterilized for repeat usage.

Figure 8:
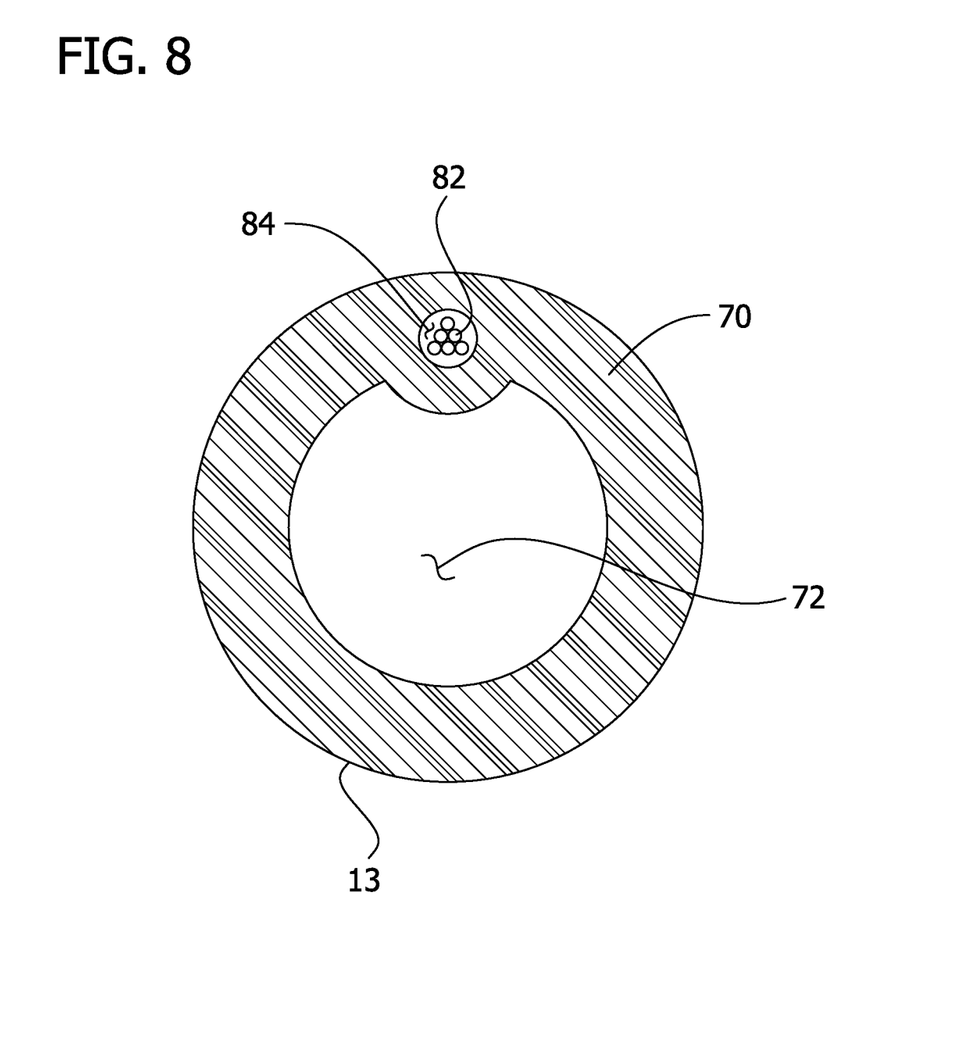
FIG. 8 is a schematic illustration showing an enlarged cross section view of a feeding tube of the feeding tube assembly, in accordance with one or more aspects of the invention.

As set forth above, the feeding tube 13 may include the imaging device 16 adjacent the distal end of the feeding tube. In the illustrated embodiment, the feeding tube 13 is a nasogastric feeding tube for insertion into a patient's stomach to deliver nutrients to the stomach. In addition to the imaging device 16, the feeding tube can include an elongate, flexible tube body 70 defining an internal feeding passage 72 extending longitudinally within the tube body (FIG. 8). The inlet adaptor 74 at the proximal end of the feeding tube 13 can be fluidly connected to the feeding passage 72. The illustrated inlet adaptor 74 may be referred to as a Y-port. During enteral feeding, the inlet adaptor 74 can be used for connection to a source of liquid nutrients, such as an enteral feeding solution. For example, a barbed connector (not shown), in fluid communication with the source of an enteral feeding solution, may be secured to the inlet adaptor 74. An outlet 76 (FIGS. 1, 9A and 9B) of the feeding passage 72 for delivering liquid nutrients directly into the patient's stomach may be adjacent the distal end of the feeding tube 13. In the illustrated embodiment, the outlet 76 includes lateral openings located proximally of the distal end of the feeding tube 13, although it is understood that the outlet may extend longitudinally through the distal end of the feeding tube. In the illustrated embodiment, the imaging device 16, including electronic components necessary for operating the imaging device, are electrically connected to a console connector 80 adjacent the proximal end of the feeding tube 13 via one or more wires or cables 82 (FIG. 8) extending longitudinally within a wire passage 84 of the feeding tube 13. The console connector 80 can be connected to a control console 86, which may include a monitor 88, via a cable 90 for viewing the images on the console. The interface cable 90 may include a control device, such as a button 92, to allow the user to record a still image, e.g., take a snapshot image, of real time video being displayed on the console 86. A suitable feeding tube 13 is disclosed in U.S. patent application Ser. No. 13/228,075, filed Sep. 8, 2011, the entirety of which is herein incorporated by reference.

Figure 9A:
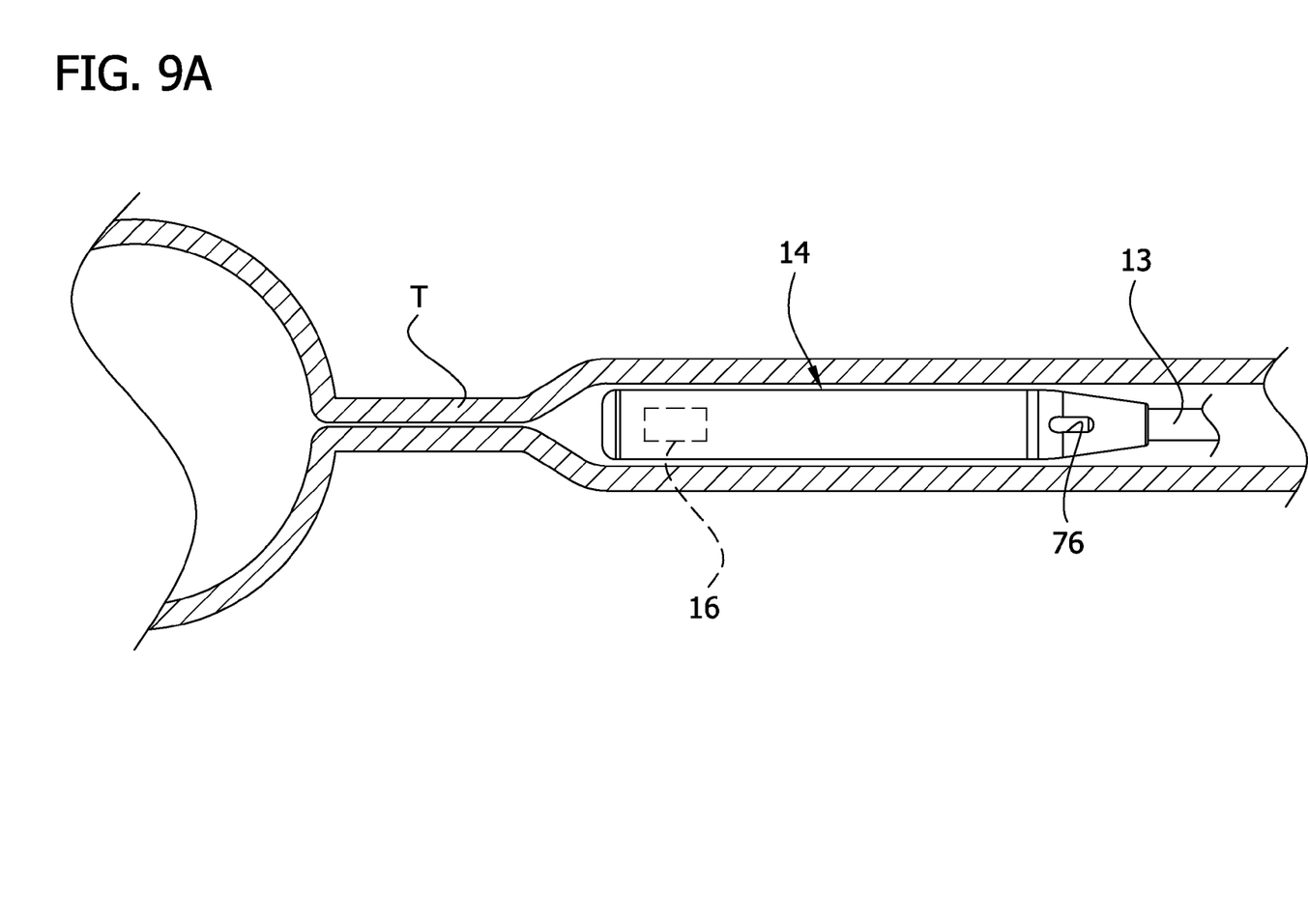
FIG. 9A is a schematic, fragmentary side view of the feeding tube assembly inserted into a subject's alimentary canal wherein the canal is in a collapsed state, in accordance with one or more aspects of the invention.
Figure 9B:
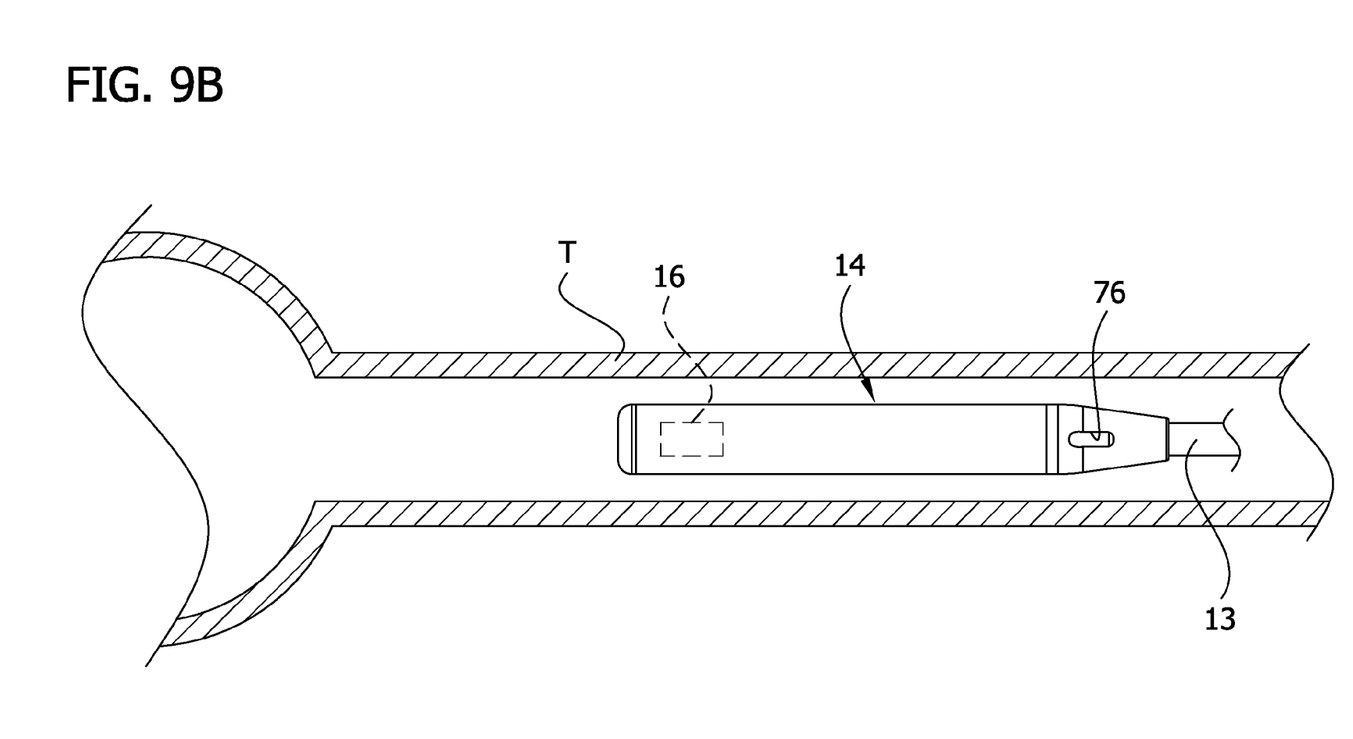
FIG. 9B is a schematic fragmentary side view of the feeding tube inserted into the subject's alimentary canal wherein the canal is insufflated by the air insufflation device, in accordance with one or more aspects of the invention.

Referring to FIGS. 9A and 9B, as set forth above, when the feeding tube 13 is at least partially inserted into the alimentary canal of a patient, the tissue T of the alimentary canal can collapse around the distal end of the feeding tube, making it difficult to acquire meaningful images of the subject's anatomy using the imaging device 16 (FIG. 9A). The images may be used for placement of the feeding tube 13. The inability to acquire meaningful images that the technician can use to judge location of the feeding tube may largely negate the benefit of having the ability to see the end of the feeding tube during placement. The air insufflation device 15 attached to the feeding tube 13 can be used to expand the tissue around the distal end of the feeding tube (i.e., insufflate the alimentary canal). To insufflate the alimentary canal, the air insufflation device 15 is attached to the feeding tube 13, such as by inserting the connector 27 into the inlet adaptor 74. With the relief valve 19 in the closed position, the bulb 13 is compressed delivering air through the conduit 23 and into the feeding passage 27 of the feeding tube 13. When the air exits the outlet 76 of the feeding passage 27 adjacent the distal end of the feeding tube 13, the air impinges on the tissue of the alimentary canal, causing the portion of the alimentary canal adjacent the distal end of the feeding tube 13 to expand (FIG. 9B). Expansion of the alimentary canal allows the imaging device 16 to acquire meaningful images of the alimentary canal at the distal end of the feeding tube. The air insufflation device 15 can be attached to the feeding tube 13 after the feeding tube is inserted into the alimentary canal or prior to inserting the feeding tube into the alimentary canal. In both instances, the device 15 can be used as a handle for manipulating the feeding tube 13. In this sense, the air insufflation device 15 can have a one-handed configuration which allows a clinician to operate both the feeding tube 13 and the insufflation device with a single hand.

The relief valve 19 can be used to selectively adjust the expansion of the tissue of the alimentary canal, which may be advantageous in both acquiring images having different vantage points, and reducing access pressure in the alimentary canal that may cause discomfort for the patient. Rotation of the cap 57 of the relief valve 19 to unseat the valve member 55 permits air to be vented out of the alimentary canal to depressurize the alimentary canal. During this process, air can flows back through the feeding tube 13 into the conduit 23 and into the fluid delivery passage 53 and valve passage 51 of the relief valve 19. Unseating the valve member 55 places the valve passage 51 in communication with atmosphere so that the air can be vented out of the relief valve 19 to the surrounding environment.

Having described the invention in detail, it will be apparent that modifications and variations are possible without departing from the scope of the invention defined in the appended claims. As various changes could be made in the above constructions and methods without departing from the scope of the invention, it is intended that all matter contained in the above description and shown in the accompanying drawings shall be interpreted as illustrative and not in a limiting sense.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. A feeding tube assembly for insertion and delivery of nutrients into an alimentary canal of a subject, comprising:
    a feeding tube having opposite proximal and distal ends, an inlet at the proximal end for connection to a source of liquid nutrients, a feeding passage defined therein and extending between the proximal and distal ends and in fluid communication with the inlet, an outlet proximate the distal end and in fluid communication with the feeding passage and the inlet, and a port separate from the inlet and disposed at the proximal end and in fluid communication with the outlet through the feeding passage;
    an air insufflation device fluidly connectable to the port, comprising a compressible air bulb having a bulb inlet and a bulb outlet; an inlet check valve disposed at the bulb inlet to unidirectionally allow air to flow into the bulb, and a relief valve fluidly connected to the bulb outlet, actuation of the air insufflation device causing air to flow through the feeding passage and exit the outlet of the feeding tube; and
    an imaging assembly configured to acquire images of the alimentary canal secured to the feeding tube proximate the distal end thereof, the air insufflation device being configured to insufflate the alimentary canal to at least partially expand the alimentary canal and aid the imaging assembly in acquiring images of the at least partially expanded alimentary canal.

2. The feeding tube assembly of claim 1, further comprising:
    an outlet check valve disposed at the bulb outlet to unidirectionally allow air to flow from the bulb;
    a conduit comprising opposite first and second conduit ends, and a conduit lumen defined therein, the conduit lumen fluidly connecting the first and second conduit ends; and
    a connector connected to the second conduit end and configured to fluidly connect to the feeding tube at the port thereof, the connector comprising a plurality of ribs each extending longitudinally about an outer surface of the connector.

3. The feeding tube assembly of claim 2, wherein the relief valve has a valve member actuatable by a user for fluidly connecting the outlet to atmosphere.

4. The feeding tube assembly of claim 3, wherein the relief valve comprises a cap securable to the valve member, and wherein the relief valve is fluidly connected to the outlet through the feeding passage and the conduit.

5. The feeding tube assembly of claim 3, wherein the relief valve comprises a valve passage fluidly connectable to the conduit lumen, and wherein the valve member comprises a protrusion in the valve passage.

6. The feeding tube assembly of claim 2, further comprising an inlet adaptor at the proximal end of the feeding tube in fluid communication with the feeding passage, wherein the connector is an oral connector configured for sealed attachment to the inlet adaptor.

7. A method of facilitating use of a feeding tube assembly for insertion into an alimentary canal of a subject, the method comprising providing a feeding tube assembly comprising a feeding tube having opposite proximal and distal ends, an inlet at the proximal end for connection to a source of liquid nutrients, a feeding passage extending between the proximal and distal ends and in fluid communication with the inlet, an outlet proximate the distal end and in fluid communication with the feeding passage and the inlet, and a port separate from the inlet and disposed at the proximal end and in fluid communication with the outlet through the feeding passage, the method further comprising providing an air insufflation device comprising a compressible air bulb having a bulb inlet and a bulb outlet, an inlet check valve disposed at the bulb inlet to unidirectionally allow air to flow into the bulb, an outlet check valve disposed at the bulb outlet to unidirectionally allow air to flow from the bulb into the port of the feeding tube assembly, and a relief valve fluidly connectable to the outlet through the feeding passage, actuation of the air insufflation device causing air to flow through the feeding passage and exit the outlet of the feeding tube, an imaging assembly configured to acquire images of the alimentary canal is secured to the feeding tube proximate the distal end thereof, the air insufflation device being configured to expand the alimentary canal to aid the imaging assembly in acquiring images of the expanded alimentary canal.

8. The method of claim 7, further comprising:
    providing a conduit having a conduit lumen defined therein, a first conduit end and an opposite, second conduit end fluidly connected to the first conduit end through the conduit lumen; and
    providing a connector comprising a plurality of ribs, each of the plurality of ribs disposed equidistantly about an outer surface of the connector, the connector configured to removably connect to the feeding tube at the port, the connector further configured to connect to the conduit.

9. The method of claim 8, further comprising connecting the connector to the conduit at the second conduit end.

10. The method of claim 9, further comprising connecting the relief valve to the conduit, wherein the relief valve comprises a valve member actuatable by a user for fluidly connecting the outlet to atmosphere.

11. The method of claim 7, further comprising providing written instructions directing disposal of the insufflation device after a single use.

12. The feeding tube assembly of claim 1, wherein the imaging assembly is configured to transmit the acquired images of the alimentary canal.

13. A method of inserting a feeding tube into an alimentary canal comprising partially inserting a feeding tube into an alimentary canal such that a distal end of the feeding tube is within the alimentary canal, insufflating the alimentary canal using an insufflation device connected to a proximal end of the feeding tube to force air down a feeding passage of the feeding tube and out a feeding outlet of the feeding tube into the alimentary canal so that the air impinges on an interior wall of the alimentary canal causing the alimentary canal to expand distally of a distal end of the feeding tube as a result of direct contact with the expelled air, acquiring an image of the alimentary canal after the alimentary canal is insufflated using an imaging assembly secured to the feeding tube proximate the distal end thereof, and further inserting the feeding tube into the alimentary canal after the canal is insufflated by the air forced by the insufflation device out of the feeding outlet into the alimentary canal and against the interior wall of the alimentary canal, and delivering liquid nutrients through the feeding passage.

* * * * *